United States Patent [19]
Cohen

[11] Patent Number: 5,853,727
[45] Date of Patent: Dec. 29, 1998

[54] PREPARATION AND USE OF INULA EXTRACTS AS A FUNGICIDE FOR THE CONTROL OF PLANT DISEASES

[75] Inventor: Yigal Cohen, Kiryat, Israel

[73] Assignee: Agrogne Ltd., Israel

[21] Appl. No.: 690,423

[22] Filed: Jul. 26, 1996

[51] Int. Cl.⁶ .................................................. A61K 35/78
[52] U.S. Cl. ........................................................ 424/195.1
[58] Field of Search .......................................... 424/195.1

[56] References Cited

U.S. PATENT DOCUMENTS

| | | | |
|---|---|---|---|
| 4,254,112 | 3/1981 | Debat et al. | 424/195.1 |
| 5,176,913 | 1/1993 | Honerlagen et al. | 424/195.1 |

OTHER PUBLICATIONS

Qasem, J.R. et al. "Antifungal Activity of Clammy Inula (*Inula Viscosa*) on *Helminthosporium Sativum and Fusarium Axysporum F. Sp. Lycopersici*", Phytopath. Medit., vol. 34, pp. 7–14, 1995.

Yegen, O, Et al, "Investigations on the Fungitoxicity of Extracts of Six Selected Plants from Turkey Against Phytopathogenic Fungi", J. Plant Dis. & Prot., 99(4), pp. 349–359, (1992).

Shao, Y. Et al. "Kaurane Glycosides from *Inula Britannica*", Phytochem., vol. 42, No. 3, pp. 783–786 (1986).

Ziv O., "Using Extracts of *Inula Viscosa* for Controlling Plant Diseases on Fresh and Dry Postharvest Products", Phytoparasitica, 24:2, p. 154 (1996).

Grande, T. Et al. "Triterpenoids from *Dittrichia Viscosa*", Phytochem., vol. 31, No. 5, pp. 1826–1828, (1992).

Gulacti, T. Et al, "Structurally Related Guaianolides from *Inula Thapsoidies*", Phytochem., vol. 40, No. 4, pp. 1717–1722 (1995).

Sanz, J. Et al. "Oxygenated Nerolidol Esters and Eudesmane Acids from *Inula Viscosa*", Phytochem., vol. 30, No. 11, pp. 3653–3655 (1991).

Gulacti, T. Et al, "Cytotoxic and Antibacterial Sesquiterpenes from *Inula Graveolens*", Phytochem., vol. 33, No. 2, pp. 407–410 (1993).

Bing–Nan, Z. Et al, "Sesquiterpene Lactones from *Inula Salsoloides*", Phytochem,. vol. 36, No. 3, pp. 721–724, (1994).

Shtacher, G. Et al, "12–Carboxyeudesma–3, 11(13)–diene", J. Med. Chem., vol. 13, No. 6 pp. 1221–1223 (1970).

Bohlmann, F. Et al, "Neue Inhaltsstoffe aus *Inula Viscosa Ait*", Verlag Chemie, Jan., 1977, pp. 1330–1334.

Sevil, O., et al, "A Eudesmanolide and Other Constituents from *Inula Graveolens*", Phytochem., vol. 31, No. 1, pp. 195–197 (1992).

*Primary Examiner*—Chhaya D. Sayala
*Attorney, Agent, or Firm*—Gifford, Krass, Groh, Sprinkle, Patmore, Anderson & Citkowski, P.C.

[57] ABSTRACT

Rapid, convenient and inexpensive methods for extracting fungicidal compounds from Inula are described, as well as methods for controlling fungal disease in crops by using these extracts. One preferred method of extraction starts with the dipping of leaves and stems of freshly cut Inula shoots for 10–15 seconds in organic solvent, at a ratio of 0.3–0.6 kg of shoots per 1 liter of solvent. A second method of extraction starts by shaking freshly cut Inula shoots in an organic solvent for 30 minutes at a ratio of 0.1–0.3 kg shoots per 1 liter of solvent. A third method is the same as the second, except that dried and ground Inula shoots are used a ratio of 0.05–0.25 kg dried shoots per 1 liter of solvent. For all three extraction methods, the solvent is evaporated and the residual paste (about 0.6–6.6% yield in the first method, 1.6–6.2% yield in the second method and 3.5–30% yield in the third method) is dissolved in acetone. The acetone solution is sprayed onto the foliage of potato, tomato, cucumbers, wheat and barley. The control of various fungal diseases, including downy mildews, gray mold, late blight, and powdery mildews, is demonstrated.

19 Claims, No Drawings

PREPARATION AND USE OF INULA EXTRACTS AS A FUNGICIDE FOR THE CONTROL OF PLANT DISEASES

FIELD AND BACKGROUND OF THE INVENTION

The present invention relates to fungicides and, more particularly, to fungicidal plant extracts from Inula species, which are effective against fungal plant infections.

Extracts of plants which are members of the Inula species are effective against infections of plants caused by a variety of fungi. These extracts are prepared by dipping freshly cut Inula shoots in an organic solvent, or agitating freshly cut or dried Inula shoots in an organic solvent, blowing off the solvent so that a paste is formed, and then dissolving this paste in an organic solvent or in water with an additive. The resultant solution is then applied to plants, resulting in the control of a wide variety of fungal diseases. Extracts of Inula plants are effective at low concentrations, in the fractions of a single percent of extract, so that dilute concentrations have excellent fungal-control properties.

The plants which are the basis of these fungicidal extracts are *Inula viscosa* and *Inula graveolens* (Family Compositae), perennial weeds widespread in the Mediterranean basin.

Methods of preparing aqueous extracts from various parts of the Inula plant are well known in the literature. By contrast, the present invention uses organic solvents. Furthermore, as shown below in Examples 2, 10 and 11, aqueous extracts are not as fungicidally effective as extracts prepared according to the present invention.

Methods have also been described which use organic solvents to extract Inula plants, but these can be clearly distinguished from the present invention. Two of these methods involve contacting the whole Inula plant, or the aerial parts thereof, with an organic solvent either by maceration of the plant in the solvent, or by percolation of the solvent through the plant. Furthermore, U.S. Pat. No. 4,254,112 to Debat et al. (hereinafter referred to as "Debat") describes the preparation of extracts of *Inula viscosa* and *Inula graveolens* with whole Inula plants which have been dried and ground, and organic solvents, by using a Soxhlet apparatus for at least 4 hours. The yield of paste obtained was 1.75–4%. U.S. Pat. No. 5,176,913 to Honerlagen et al. (hereinafter referred to as "Honerlagen") describes a process for preparing a partial extract from roots of *Inula helenium* which involves contacting the plant material with an organic solvent, adding a drying agent to the solution to remove the water, removing this drying agent and then distilling the dried organic phase. By contrast, the method of the present invention involves either briefly dipping the leaves and stems of the shoots of *Inula viscosa* or *Inula graveolens* into an organic solvent or shaking the freshly cut or dried and ground leaves and stems of the shoots in an organic solvent for 30 minutes, and then evaporating the solvent to form a paste. Furthermore, the yield of paste obtained by these methods is as much as 30%, in contrast to the low yields known in the literature.

The medicinal properties of Inula extracts in humans are well known. For example, Debat disclosed the antimicrobial activity of extracts of Inula for use in human beings. However, the fungicidal effects of Inula extracts have only been demonstrated on fungi growing in petri dishes or on post-harvest fruits. For example, Qasem et al. (*Phytopathologia Mediterrana* 34:7–14, 1995) demonstrated that the growth of certain fungi in petri dishes was inhibited by aqueous extracts of *Inula viscosa* as well as by dried plant material added directly to the fungal growth media. By contrast, the method of the present invention uses Inula extracts prepared with organic solvents against fungal infections of crop plants themselves.

Clearly, although Inula extracts have been shown to have fungicidal activity in the petri dish, the methods of preparation for these extracts have not been sufficient for large-scale use directly on crop plants. The true effectiveness of these extracts against fungal infections of plants is therefore unknown. Furthermore, there is a clear need for better methods to prepare Inula extracts. Qasem et al. (Ibid, page 13, 1995) concluded: "The diversity in the methodology of extraction and the differences in the results obtained . . . increased the need for developing more efficient, convenient and cheaper methods of extraction to facilitate more extensive utilization of fungicidal extracts, especially if greater quantity of extracts must be prepared for large-scale production".

There is thus a widely recognized need for, and it would be highly advantageous to have, a method or methods for preparing extracts of plants of the Inula species which would facilitate the large-scale use of these extracts, as well as methods for using these extracts to control fungal infections in crop plants.

SUMMARY OF THE INVENTION

According to the present invention there is provided a method for preparing an extract of Inula species which comprises (a) contacting shoots of the species with an organic solvent to form a solution and debris; (b) removing the debris from the solution; and (c) evaporating the solution to form a paste.

In a preferred embodiment, the starting material is the leaves and stem of the upper, younger part of the shoots, the upper part of the shoot extending from about 20 to about 40 cm from the tip of the shoot. The flowers are not used. Hereinafter the term "shoot" shall be used to denote the leaves and stem of the shoot of the Inula plant.

In a more preferred embodiment, the solvent used is taken from the group which includes, but is not limited to, n-hexane, chloroform, acetone, ethylacetate, diethylether, ethanol, methanol, or their mixtures thereof.

In another more preferred embodiment, the specific species of the Inula plant which are used are *Inula viscosa* and *Inula graveolens*.

In yet another more preferred embodiment, the paste is dissolved in an organic solvent. Alternatively, the paste is dissolved in water with an additive, such as an appropriate emulsifier or emulsifiers, or an additional appropriate adjuvant or adjuvants.

In a still more preferred embodiment, an extract of freshly cut shoots of Inula is prepared by briefly dipping the whole shoots in an organic solvent for from about 10 to about 15 seconds. The organic solvent is taken from the group which includes, but is not limited to, n-hexane, chloroform, acetone, ethylacetate, diethylether or their mixtures thereof. The extraction can be carried out by using a ratio of volume of organic solvent to weight of the shoots of about one liter of organic solvent to from about 300 to about 600 g of freshly cut shoots. After the extraction, the shoots are discarded, the resultant extract is filtered through paper to remove debris from the solution and the solvent is evaporated by either a stream of air in a hood, or under reduced pressure at 37° C. The product thus obtained is a colorless, brown-yellow or yellow paste with no water residues. This paste is then weighed and dissolved in an organic solvent taken from the group which includes, but is not limited to, n-hexane, chloroform, acetone, ethylacetate, diethylether or their mixtures thereof. Alternatively, the paste can be dissolved in water with the aid of an additive, such as an appropriate emulsifier or emulsifiers, or an additional appropriate adjuvant or adjuvants.

In a second preferred embodiment, the method of extraction also starts with freshly cut shoots of Inula species. These freshly cut shoots are shaken in an organic solvent for about 30 minutes at 120 rpm at room temperature, in a ratio of volume of the organic solvent to the weight of the shoots of about one liter of the organic solvent to from about 100 to about 300 g of freshly cut shoots, without first homogenizing the shoots. The solvent is taken from the group which includes, but is not limited to, n-hexane, chloroform, acetone, ethylacetate, diethylether, ethanol, methanol or their mixtures thereof. The resultant extract is filtered through paper to remove the debris from the solution, and the solvent is then evaporated by either a stream of air in a hood, or under reduced pressure at 37° C. The product thus obtained is a colorless, brown-yellow or yellow paste with no water residues. This paste is then weighed and dissolved in an organic solvent taken from the group which includes, but is not limited to, n-hexane, chloroform, acetone, ethylacetate, diethylether, ethanol, methanol or their mixtures thereof. Alternatively, the paste can be dissolved in water with the aid of an additive, such as an appropriate emulsifier or emulsifiers, or an additional appropriate adjuvant or adjuvants.

In a third preferred embodiment, the method of extraction is similar to the above second method, except that the starting material is dried and ground Inula shoots. These dried and ground shoots are shaken in an organic solvent for about 30 minutes at 120 rpm at room temperature, in a ratio of volume of organic solvent to weight of dried and ground shoots of about one liter of organic solvent to from about 50 to about 250 g of dried and ground shoots. The solvent is taken from the group which includes, but is not limited to, n-hexane, chloroform, acetone, ethylacetate, diethylether, ethanol, methanol or their mixtures thereof. The resultant extract is filtered through paper to remove the debris from the solution, and the solvent is then evaporated by either a stream of air in a hood, or under reduced pressure at 37° C. The product thus obtained is a colorless, brown-yellow or yellow paste with no water residues. This paste is then weighed and dissolved in an organic solvent taken from the group which includes, but is not limited to, n-hexane, chloroform, acetone, ethylacetate, diethylether, ethanol, methanol or their mixtures thereof. Alternatively, the paste can be dissolved in water with the aid of an additive, such as an appropriate emulsifier or emulsifiers, or an additional appropriate adjuvant or adjuvants.

According to this invention there is also provided a method for protecting plants against fungal infections, comprising the steps of (a) preparing an extract of Inula species by (i) contacting shoots of the species with an organic solvent to form a solution and debris; (ii) removing the debris from the solution; (iii) evaporating the solution to form a paste; and (iv) dissolving the paste in a carrier to form a fungicidal composition; and (b) applying a fungicidally effective amount of the fungicidal composition to a plant for protecting against fungal infection.

In yet another embodiment, the preferred concentration of paste in a carrier used in the method for protecting plants against fungal infections ranges from about 0.01 to about 1 percent by weight of paste per volume of carrier. Solutions containing the Inula extract are sprayed onto the upper leaf surfaces of various crop plants for the control of fungal plant infections, including but not limited to diseases caused by fungi of the Oomycetes, Ascomycetes and Fungi imperfecti classes.

The method of the invention is particularly suitable for use against fungi of the Oomycetes, Ascomycetes and Fungi imperfecti classes including but not limited to *Cladosporium cucumerinum, Phytophthora infestans, Botrytis cinerea, Pseudoperonospora cubensis, Sphaerotheca fuliginea, and Erysiphe graminis* in crops including but not limited to grapevines, tomato, wheat, barley, tobacco, potato, onions, cucurbits or crucifers. It should be noted that according to *Fungicides in Plant Disease Control* (Y. L. Nene and P. N. Thapliyal, International Science Publishers, New York, N.Y., USA, 1993), the effective spectrum of activity of a fungicide encompasses entire classes of fungi. If a fungicide is effective against one member of a class, it usually will be effective against other members of that class. Furthermore, if fungi from the same class infect different plants, the same fungicide will be effective against the disease in all the different plants, since fungicides are disease-specific rather than plant-specific.

DESCRIPTION OF THE PREFERRED EMBODIMENTS

The present invention is of a method for preparing extracts of Inula species and of a method for using these extracts to protect plants against fungal infections.

The invention is illustrated by the following examples, which describe the preparation and use of Inula extracts against fungal infections in plants.

To test the efficacy of these extracts, experiments were performed in which plants were sprayed using a fine glass atomizer, with either Inula extract or pure solvent as a control. Treated and control plants were then inoculated with a crop-respective fungal pathogen. After an incubation period the extent of the infection was measured. Unless otherwise stated, percentage protection from the disease due to the treatment with the Inula extract was calculated as:

% control of the disease=[1-(% infection in treated plants/% infection in control plants)]×100

EXAMPLE 1

Methods of Preparation of Inula Extracts Against Fungal Infections in Plants

Method 1: Briefly Dipping Freshly Cut Shoots in an Organic Solvent

Freshly cut leaves and stems of the upper parts of *Inula viscosa* and *Inula graveolens*, preferably the section extending 20–40 cm from the tip of the shoot, were briefly dipped in an organic solvent for 10–15 seconds. One liter of solvent was used per 300–600 g of shoots. The solvent used was selected from the group including n-hexane, chloroform, acetone, diethylether or ethylacetate. After dipping, the plant material was discarded, the extract was filtered through paper and the solvent was evaporated by a stream of air or under reduced pressure at 37° C. A paste was obtained with no water residues.

The yields of paste obtained are given in Table 1. The yield ranges between 4.50–6.64 g of paste per 100 g of freshly cut shoots, with the exception of n-hexane, which yielded 0.55 g paste per 100 g of freshly cut shoots. To obtain the data in Table 1, 100 g of freshly cut shoots were used in 0.25 liter of solvent.

Method 2: Shaking Freshly Cut Shoots for 30 Minutes

The freshly cut shoots as described in Method 1 above were placed in an organic solvent and shaken for 30 minutes at 120 rpm at room temperature. One liter of solvent was used per 100–300 g of freshly cut shoots. The solvent was selected from the group including n-hexane, chloroform, acetone, ethylacetate, diethylether, ethanol or methanol. Water extraction was performed as a control. After extraction the debris was removed by filtration and the solvent was evaporated as in Method 1 above. The yields of paste obtained are given in Table 1. Extract processed with water gave the lowest yield, only 0.96 g of paste per 100 g of freshly cut Inula shoots. The second lowest yield was obtained with n-hexane, giving 1.60 g of paste per 100 g of freshly cut shoots. Other solvents yielded 4.00–6.24 g of paste per 100 g of freshly cut shoots. The highest yield, 6.24 g of paste per 100 g of freshly cut shoots, was obtained with ethylacetate. To obtain the data in Table 1, 100 g of shoots were used in 1 liter of solvent.

Method 3: Shaking Dried, Ground Shoots for 30 Minutes

Freshly cut shoots as described in Method 1 were placed under blowing air at room temperature for one day until dry. The water content of these dried shoots was 8–10%, while freshly cut shoots contained 58–60% water. These dried shoots were crushed, placed in an organic solvent or water as a control and then shaken for 30 minutes at 120 rpm at room temperature. The organic solvent was selected from the group including n-hexane, chloroform, acetone, ethylacetate, diethylether, ethanol or methanol. One liter of solvent was used per 50–250 g of dried, ground shoots. After extraction, the plant material was removed by filtration of the solution through paper. The solvent was evaporated as in Method 1 above.

The yields of paste obtained are given in Table 1. The lowest yield was obtained with n-hexane, 3.52 g of paste per 100 g dried, ground shoots. The second lowest yield was obtained with water, 12.8 g of paste per 100 g dried, ground shoots. The other solvents yielded 14.4–28.76 g of paste per 100 g of dried, ground shoots. To obtain the data in Table 1, 10 g of dried and ground shoots were used with 0.1 liter of solvent.

TABLE 1

Yield of different methods of preparing Inula extracts

| Solvent | Dry weight of extract (grams per 100 g starting material) Extraction Procedure | | |
|---|---|---|---|
| | Freshly cut shoots, dipping for 10 sec* | Freshly cut shoots, shaking for 30 min** | Dried shoots, shaking for 30 min*** |
| Water | — | 0.96 | 12.80 |
| Methanol | — | 4.48 | 29.76 |
| Ethanol | — | 4.96 | 20.80 |
| Acetone | 5.04 | 4.80 | 19.84 |
| Ethylacetate | 4.87 | 6.24 | 22.08 |
| Diethylether | 4.50 | 4.00 | 14.40 |
| Chloroform | 6.64 | 4.64 | 16.00 |
| n-Hexane | 0.55 | 1.60 | 3.52 |

*100 g freshly cut shoots extracted in 0.25 liter of solvent
**100 g freshly cut shoots extracted in 1 liter of solvent
***10 g dried and ground shoots extracted in 0.1 liter of solvent

EXAMPLE 2

The Fungicidal Effects of Components of Inula Extracts After Separation by Thin-layer Chromatography Inula extracts were prepared according to Method 1, using 100 g of freshly cut shoots of *Inula viscosa* in 0.25 liter of chloroform, acetone, ethylacetate, diethylether or n-hexane. 0.55–6.64 g of paste was obtained. The paste was dissolved in the original solvent to form a 4% solution, percentage by weight.

Extracts were also prepared according to Method 3, using 10 g of dried, ground *Inula viscosa* shoots in 0.1 liter of water, methanol, ethanol, chloroform, acetone, ethylacetate, diethylether or n-hexane. 3.52–29.76 g of paste were obtained. The paste was dissolved in the original solvent to form a 4% solution, percentage by weight.

Twenty microliters (0.02 ml) of each of the solutions were spotted on a silica-gel plate for thin-layer chromatography (TLC). The TLC plates were run in chloroform: methanol 90:10 (v/v) and then developed to determine the number and intensity of components with fungicidal action. Plates were developed either by using iodine vapor ($I_2$) or by overlaying the TLC plate with a conidial suspension of the fungus *Cladosporium cucumerinum* in 1 % potato dextrose broth, and then incubating the plate in a moist box at 25° C. for 3 days. In both cases, the $R_f$ value for each spot was measured. The numerical results of the fungicidal activity of the Inula extracts prepared with chloroform according to Method 1 are summarized in Table 2.

Using Method 1, the chloroform extract gave 10 spots with iodine vapor, of which 7 were inhibitory to *C. cucumerinum*. Similar results were seen after using Method 1 with the other solvents, except water and n-hexane. n-Hexane yielded only 3 inhibitory compounds (compounds 7, 8 and 9), which had an $I_2$ staining intensity of ++ and inhibited growth zones of 8–10 mm. Similar results were seen using *I. graveolens*.

TABLE 2

Results of thin-layer chromatography separation and bioassay of the fungicidal properties of Inula extract

| Compound Number | $R_f$ of Compound* | $I_2$ Staining Intensity | Width of Zone of Inhibited Growth of *C. cucumerinum* (mm) |
|---|---|---|---|
| 1 | 0.00 | − | 0 |
| 2 | 0.31 | + + | 7 |
| 3 | 0.35 | + + | 0 |
| 4 | 0.37 | + + | 0 |
| 5 | 0.42 | + + | 5 |
| 6 | 0.49 | + + + | 11 |
| 7 | 0.53 | + + + + | 15 |
| 8 | 0.64 | + + + + | 10 |
| 9 | 0.72 | + + + + | 15 |
| 10 | 0.81 | + | 3 |

*Note: $R_f$ values may vary ± 10% between experiments

When Method 3 and the solvents acetone, diethylether, chloroform and ethylacetate were used, the results obtained were identical to those shown in Table 2 for Method 1 with chloroform. Ethanol and methanol also produced identical results, except that compound 1 had an intensity of + and ++, respectively. Also, compound 1 produced by ethanol showed no inhibition of *C. cucumerinum*. Extracts prepared with n-hexane according to Method 3 produced similar results as extracts prepared according to Method 1: only three inhibitory compounds were produced (compounds 7, 8 and 9). Extracts prepared with water according to Method 3 only produced compounds 1 and 9, with $I_2$ staining intensities of +++ and ±, respectively. Compound 1 showed no inhibitory effect on the growth of *C. cucumerinum*, while compound 9 had a slight effect, with an inhibitory zone of 4 mm. Similar results were seen with *I. graveolens*.

EXAMPLE 3

The Effect of Inula Extracts on Fungal Growth in vitro

Inula extract was prepared according to Method 1, with 100 g of freshly cut shoots of *Inula viscosa* or *Inula graveolens* and 0.5 liter of chloroform. The yield was 7 g of paste, which was dissolved in acetone, and then diluted in acetone to form 0.01–1 % solution. Ten μl droplets of solutions in acetone with various concentrations of Inula extract were pipetted into depressions of microscope glass slides, the solvent evaporated instantly, and 10 μl sporangial suspension of the fungus *Phytophthora infestans* and conidia of *Botrytis cinerea* added. Slides were incubated for 20 hours at 15° C. and 25° C., respectively, while sitting on wet filter paper enclosed in petri dishes. The percentage germination of the spores was then evaluated using a microscope. Results are presented in Table 3, using extract of *I. viscosa*. Similar results were seen for *I. graveolens*.

TABLE 3

The effect of Inula extract on zoospore discharge and cytospore germination of *Phytophthora infestans*, and spore germination of *Botrytis cinerea*.

| | Concentration of Inula extract (%) | | |
|---|---|---|---|
| | *P. infestans* | | *B. cinerea* |
| Inhibition of Fungal Activity (%) | Zoospore Discharge | Cytospore Germination | Conidial Germination |
| 50% Inhibition | 0.075 | 0.05 | 0.1 |
| 100% Inhibition | 0.2 | 0.1 | 0.3 |

EXAMPLE 4

The Effect of Inula Extract Against Potato Late Blight

The extract was prepared as described in Example 3 and then sprayed, at various concentrations, onto the upper leaf surfaces of 5 week old potato plants. Acetone alone was sprayed as control. Plants were inoculated 1 day later with sporangia of *Phytophthora infestans*, placed in a dew chamber overnight to ensure infection, and then placed in a growth chamber at 20° C. for 7 days. The protection against late blight caused by *P. infestans* is presented in Table 4, using *I. viscosa*. Similar results were seen with *I. graveolens*.

TABLE 4

The protective effect of Inula extract on late blight development in potato

| Concentration of Inula Extract (%) | Blighted Leaf Area (%) | Protection Against Blight (%) |
|---|---|---|
| 0 (acetone control) | 100 | 0 |
| 0.00125 | 86 | 14 |
| 0.0250 | 80 | 20 |
| 0.05 | 60 | 40 |
| 0.1 | 50 | 50 |
| 0.2 | 35 | 65 |
| 0.4 | 5 | 95 |

EXAMPLE 5

The Effect of Inula Extract Against Downy Mildew in Cucumber

The extract was prepared as described in Example 3 and sprayed as described in Example 4 onto the upper leaf surfaces of 3 week old cucumber plants. After one day, the sprayed plants were inoculated with sporangia of *Pseudoperonospora cubensis*, which is the causal agent of downy mildew in cucurbits. Plants were incubated under the same conditions described in Example 4. Results are shown in Table 5, using *I. viscosa*. Similar results were seen with *I. graveolens*, within ±5% of inhibition of disease spread.

TABLE 5

The protective effect of Inula extract against *Pseudoperonospora cubensis* in cucumbers.

| Concentration of Inula Extract (%) | Mildewed Leaf Area (%) | Protection Against Downy Mildew (%) |
|---|---|---|
| 0 (acetone control) | 78 | 0 |
| 0.00125 | 58 | 26 |
| 0.0250 | 45 | 42 |
| 0.05 | 38 | 51 |
| 0.1 | 25 | 68 |
| 0.2 | 13 | 83 |
| 0.4 | 3 | 96 |

EXAMPLE 6

The Effect of Inula Extract Against Powdery Mildew in Cucumber

Cucumber plants were treated in the same manner described in Example 5 except that the plants were inoculated with the fungus *Sphaerotheca fuliginea* which causes powdery mildew disease in cucurbits. Results are presented in Table 6, using *I. viscosa*. Similar results were obtained with *I. graveolens*.

TABLE 6

The protective effect of Inula chloroform extract against powdery mildew caused by *Sphaerotheca fuliginea* in cucumber plants.

| Concentration of Inula Extract (%) | Mildewed Leaf Area (%) | Protection Against Powdery Mildew (%) |
|---|---|---|
| 0 (acetone control) | 60 | 0 |
| 0.25 | 35 | 42 |
| 0.5 | 15 | 75 |
| 1.0 | 0 | 100 |

EXAMPLE 7

Effect of Inula Extract Against Gray Mold

This example was carried out with cucumber plants in the same manner described in Example 6 except that younger plants at cotyledonary stage growth were inoculated with conidia of the fungus *Botrytis cinerea*, which causes gray mold. Results are given in Table 7, using *I. viscosa*. Similar results were obtained using *I. graveolens*.

TABLE 7

The protective effect of Inula extract against gray mold caused by
*Botrytis cinerea* in cucumber plants.

| Concentration of Inula Extract (%) | Alive Plants (%) |
|---|---|
| 0 (acetone control) | 0 |
| 0.25 | 40 |
| 0.5 | 70 |
| 1.0 | 100 |

EXAMPLE 8

Effect of Inula Extract Against Powdery Mildew in Wheat and Barley

The extract was prepared as described in Example 3 and sprayed onto young, 1-leaf stage, wheat or barley plants. Plants were dusted, 1 day later, with conidia of the fungi *Erysiphe graminis* f.sp. *tritici* on wheat, and *E. graminis* f.sp. *hordei* on barley. Both fungi cause powdery mildew disease on their host. Results are shown in Table 8, using *I. viscosa*. Similar results were obtained with *I. graveolens*.

TABLE 8

The protective effect of Inula extract against powdery mildew in wheat and barley.

| Concentration of Inula Extract (%) | Mildewed Leaf Area (%) | | Protection Against Powdery Mildew (%) | |
|---|---|---|---|---|
| | Wheat | Barley | Wheat | Barley |
| 0 (acetone control) | 92 | 80 | 0 | 0 |
| 0.05 | 3 | 5 | 97 | 94 |
| 0.1 | 0 | 0 | 100 | 100 |
| 0.2 | 0 | 0 | 100 | 100 |

EXAMPLE 9

Protective Effect of Extracts Prepared by Dipping Freshly Cut Shoots

Inula extracts were prepared according to Method 1, using 100 g of freshly cut Inula shoots and 0.25 liter of either chloroform, acetone, ethylacetate or n-hexane. The paste obtained was dissolved in acetone to form a 0.25% solution, percent by weight. The various solutions were sprayed on potato, cucumber and wheat plants, which were then inoculated with the appropriate fungal pathogen and incubated for 7 days. Results are shown in Table 9, using *I. viscosa*. Similar results were obtained using *I. graveolens*.

TABLE 9

Protection of crop plants by extracts made according to Method 1.
% Control of the Disease

| Solvent Used for Extraction | Potato Late Blight | Cucumber Downy Mildew | Cucumber Powdery Mildew | Wheat Powdery Mildew |
|---|---|---|---|---|
| Chloroform | 100 | 93 | 90 | 89 |
| Acetone | 94 | 95 | 65 | 96 |
| Ethylacetate | 96 | 98 | 75 | 98 |
| n-Hexane | 96 | 88 | 95 | 100 |

EXAMPLE 10

Protective Effect of Inula Extracts Prepared by Shaking Freshly Cut Shoots

Inula extracts were prepared according to Method 2, using 100 g of freshly cut Inula shoots and 1.0 liter of either water, chloroform, methanol, ethanol, diethylether, acetone or ethylacetate. A sample of the extract was evaporated to dryness and weighed. The remaining extract was sprayed on potato plants, which were then inoculated with *P. infestans* one day later and incubated for 7 days. Results are presented in Table 10, using *I. viscosa*.

TABLE 10

Protection of potato plants against late blight by extracts made according to Method 2.

| Solvent Used for Extraction | Concentration of Paste (%) | Control of Disease (% Inhibition) |
|---|---|---|
| Water | 0.12 | 0 |
| Methanol | 0.56 | 96 |
| Ethanol | 0.62 | 97 |
| Acetone | 0.60 | 94 |
| Ethylacetate | 0.78 | 95 |
| Diethylether | 0.50 | 97 |
| Chloroform | 0.58 | 90 |

EXAMPLE 11

Protective Effect of Inula Extracts Prepared by Shaking Dried, Ground Shoots

Extract of Inula was prepared according to Method 3 with 10 g of dried and ground shoots of *Inula viscosa* in 0.1 liter of water or an organic solvent such as methanol, ethanol, acetone, ethylacetate, diethylether, n-hexane or chloroform. A sample of the resultant extract was dried and weighed. The remaining extract was diluted with acetone for the organic solvents, or water for the aqueous extract, so as to obtain a 0.4% solution. The solutions were sprayed on potato, cucumber and wheat plants. Plants sprayed with either water for the aqueous extract or pure acetone for the organic solvents served as controls. Treated and control plants were thereafter inoculated, potato with *Phytophthora infestans*, cucumbers with *Pseudoperonospora cubensis* or with *Botrytis cinerea* and wheat with *Erysiphe graminis tritici*. Results are presented in Table 11, for *I. viscosa*. Similar results were obtained using *I. graveolens*.

TABLE 11

Protection against plant diseases by extracts of dried, ground Inula shoots prepared according to Method 3.

| Solvent Used for Extraction | % Control of the Disease | | | | |
|---|---|---|---|---|---|
| | Late Blight in Potato | Downy Mildew in Cucumber | Powdery Mildew in Wheat | Powdery Mildew in Cucumber | Gray Mold in Cucumber |
| Water | 26 | 43 | 45 | 37 | – |
| Methanol | 89 | 99 | 90 | 75 | – |
| Ethanol | 94 | 99 | 93 | 95 | – |
| Ethylacetate | 91 | 91 | 83 | 100 | – |
| Acetone | 99 | 95 | 93 | 75 | 100 |
| Chloroform | 83 | 100 | 86 | 70 | – |
| n-Hexane | 97 | 91 | 93 | 97 | 85 |

TABLE 11-continued

Protection against plant diseases by extracts of dried, ground Inula shoots prepared according to Method 3.

| Solvent Used for Extraction | % Control of the Disease | | | | |
|---|---|---|---|---|---|
| | Late Blight in Potato | Downy Mildew in Cucumber | Powdery Mildew in Wheat | Powdery Mildew in Cucumber | Gray Mold in Cucumber |
| Diethylether | 96 | 91 | 93 | 95 | – |

While the invention has been described with respect to a limited number of embodiments, it will be appreciated that many variations, modifications and other applications of the invention may be made.

What is claimed is:

1. A method for preparing an extract of Inula species which comprises:
   (a) contacting whole shoots of the species with an organic solvent at room temperature for 10 to 15 seconds to form a solution and debris;
   (b) removing said debris from said solution; and
   (c) evaporating said solution to form a paste.

2. The method according to claim 1, wherein said paste is dissolved in water with an additive.

3. The method according to claim 1, wherein said paste is dissolved in an organic solvent.

4. The method according to claim 1, wherein said shoots include leaves and stems of upper parts of said Inula species.

5. The method according to claim 1, wherein said shoots are freshly cut.

6. The method according to claim 1, wherein said organic solvent includes a compound selected from the group consisting of ethylacetate, chloroform, acetone, ethanol, methanol, diethylether and n-hexane.

7. The method according to claim 1, wherein said shoots are freshly cut shoots of the species and the ratio of volume of said organic solvent to weight of the shoots is about one liter of said organic solvent to from about 100 to about 300 g of said shoots.

8. The method according to claim 1, wherein said shoots are freshly cut shoots of the species and said shoots are contacted by dipping said shoots for from about 10 to about 15 seconds in said organic solvent, said organic solvent including a compound selected from the group consisting of n-hexane, diethylether, chloroform, acetone and ethylacetate.

9. The method according to claim 8, wherein the ratio of volume of said organic solvent to weight of said shoots is about one liter of said organic solvent to from about 300 to about 600 g of said shoots.

10. The method according to claim 9, wherein said organic solvent includes chloroform.

11. The method according to claim 7, wherein said solvent includes ethanol.

12. The method according to claim 1, wherein said solvent includes acetone.

13. The method according to claim 1, wherein said solvent includes n-hexane.

14. The method according to claim 1, wherein the Inula species are *Inula viscosa* and *Inula graveolens*.

15. A method for protecting plants against fungal infections, comprising the steps of
   (a) preparing an extract of Inula species by
      (i) contacting non-homogenized shoots of the species with an organic solvent at room temperature for up to 30 minutes, to form a solution and debris;
      (ii) removing said debris from said solution;
      (iii) evaporating said solution to form a paste; and
      (iv) dissolving said paste in a carrier to form a fungicidal composition; and
   (b) applying a fungicidally effective amount of said fungicidal composition to a plant for protecting against fungal infection.

16. The method according to claim 15, wherein said plant is selected from the group consisting of grapevines, cucurbits, tomato, wheat, barley, onion, tobacco, crucifers and potato.

17. The method according to claim 15, wherein said fungal infection is caused by phytopathogenic fungi of a class selected from the group consisting of Oomycetes, Ascomycetes and Fungi imperfecti.

18. The method according to claim 17, wherein said fungal infection is caused by a fungus selected from the group consisting of *Cladosporium cucumerinum, Phytophthora infestans, Botrytis cinerea, Pseudoperonospora cubensis, Sphaerotheca fuliginea* and *Erysiphe graminis*.

19. A method for preparing an extract of Inula species which comprises:
   (a) contacting unhomogenized shoots of the species with an organic solvent at room temperature, for up to thirty minutes, so as to form a solution and debris;
   (b) removing said debris from said solution; and
   (c) evaporating said solution to form a paste.

* * * * *